United States Patent
Buchmann

(10) Patent No.: US 10,359,358 B2
(45) Date of Patent: Jul. 23, 2019

(54) METHODS FOR NON-INTRUSIVELY DETERMINING INDICATIONS OF WHOLESOMENESS OF ITEMS OF PACKAGED ALIMENT

(71) Applicant: Foss Analytical A/S, Hilleroed (DK)

(72) Inventor: Nils Bo Buchmann, Frederiksberg (DK)

(73) Assignee: Foss Analytical A/S, Hilleroed (DK)

( * ) Notice: Subject to any disclaimer, the term of this patent is extended or adjusted under 35 U.S.C. 154(b) by 0 days.

(21) Appl. No.: 15/570,539

(22) PCT Filed: May 13, 2015

(86) PCT No.: PCT/IB2015/053518
§ 371 (c)(1),
(2) Date: Oct. 30, 2017

(87) PCT Pub. No.: WO2016/181192
PCT Pub. Date: Nov. 17, 2016

(65) Prior Publication Data
US 2018/0143127 A1    May 24, 2018

(51) Int. Cl.
*G01N 21/35*     (2014.01)
*G01N 21/31*     (2006.01)
(Continued)

(52) U.S. Cl.
CPC ............... *G01N 21/31* (2013.01); *G01J 3/28* (2013.01); *G01N 21/359* (2013.01); *G01N 33/02* (2013.01);
(Continued)

(58) Field of Classification Search
CPC ...... G01N 21/31; G01N 21/359; G01N 21/35; G01N 3/28; G01N 33/02; G01N 2035/00752; G01N 2201/29
See application file for complete search history.

(56) References Cited

U.S. PATENT DOCUMENTS 5,473,161 A     12/1995   Nix et al.
6,964,191 B1 *  11/2005   Tata .................... G01N 15/082
                                                    73/38
(Continued)

FOREIGN PATENT DOCUMENTS

DE          10315541 A1    10/2004
WO    WO-2007/046280 A1     4/2007

OTHER PUBLICATIONS

International Search Report PCT/ISA/210 for International Application No. PCT/IB2015/053518 dated Jul. 7, 2015.
(Continued)

*Primary Examiner* — David P Porta
*Assistant Examiner* — Djura Malevic
(74) *Attorney, Agent, or Firm* — Harness, Dickey & Pierce, P.L.C.

(57) ABSTRACT

A non-intrusive method for determining an indication of wholesomeness of an unopened item of packaged aliment comprising the steps of illuminating an unopened item of packaged aliment with electromagnetic energy at a plurality of different wavelengths through a suitably transparent region of the packaging so as to interact with the packaged aliment; obtaining spectral information regarding the interaction of the plurality of different wavelengths with the packaged aliment as subsequent spectral information; interrogating the packaging to access original spectral information regarding a previous interaction of the plurality of wavelengths with the same unopened item of packaged aliment and associated with the packaging; comparing some or all of the subsequent spectral information with some or all of the original spectral information to obtain a measure of their spectral deviation; and determining an indication of wholesomeness of the unopened item of packaged aliment in dependence of the obtained measure of spectral deviation.

10 Claims, 1 Drawing Sheet

(51) Int. Cl.
*G01N 33/02* (2006.01)
*G01N 21/359* (2014.01)
*G01J 3/28* (2006.01)
*G01N 35/00* (2006.01)

(52) U.S. Cl.
CPC ... *G01N 21/35* (2013.01); *G01N 2035/00752* (2013.01); *G01N 2201/129* (2013.01)

(56) References Cited

U.S. PATENT DOCUMENTS

| | | | | |
|---|---|---|---|---|
| 2003/0162301 | A1* | 8/2003 | Noergaard | A61B 5/7267 436/172 |
| 2006/0032293 | A1* | 2/2006 | Wild | G01N 33/14 73/38 |
| 2006/0078658 | A1* | 4/2006 | Owens | G01N 1/24 426/231 |
| 2009/0055199 | A1* | 2/2009 | Yusuf | G06F 19/3475 705/15 |
| 2009/0141961 | A1* | 6/2009 | Smith | G06K 9/00577 382/135 |
| 2013/0112895 | A1* | 5/2013 | Birlouez-Aragon | G01N 21/6486 250/459.1 |
| 2014/0122167 | A1* | 5/2014 | Jung | G06Q 10/0637 705/7.29 |
| 2016/0086255 | A1* | 3/2016 | Sainfort | G06Q 30/0637 705/26.41 |
| 2016/0109423 | A1* | 4/2016 | Reichl | G01N 33/12 250/459.1 |
| 2016/0223508 | A1* | 8/2016 | Angres | G01N 33/14 |

OTHER PUBLICATIONS

Written Opinion of the International Searching Authority PCT/ISA/237 for International Application No. PCT/IB2015/063623 dated Jul. 7, 2015.
Raul Grau et al. "Nondestructive assessment of freshness in packaged sliced chicken breasts using SW-NIR spectroscopy". Food Research International 44. Elsevier Journal. 2011. pp. 331-327.

* cited by examiner

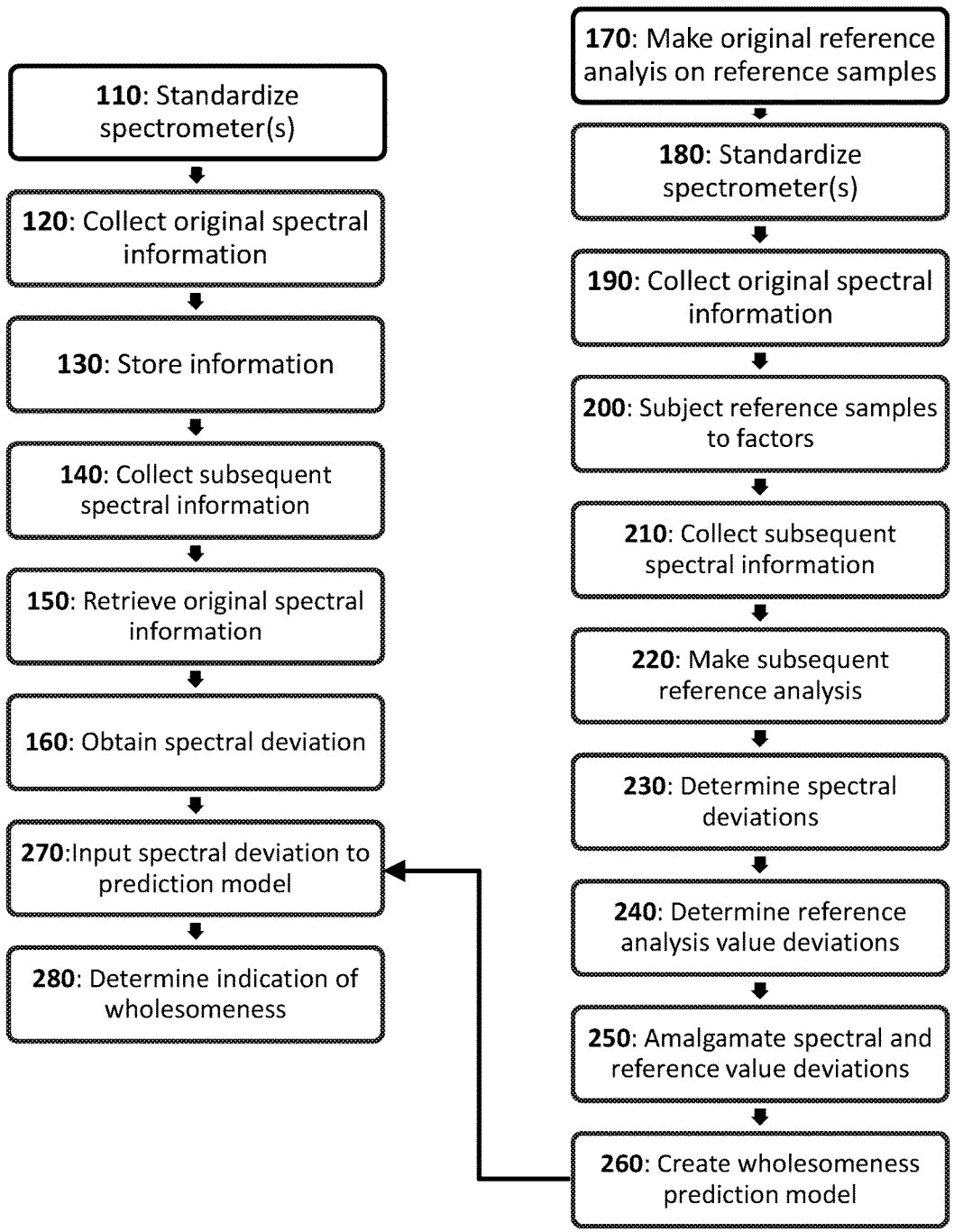

METHODS FOR NON-INTRUSIVELY DETERMINING INDICATIONS OF WHOLESOMENESS OF ITEMS OF PACKAGED ALIMENT

CROSS-REFERENCE TO RELATED APPLICATIONS

This application is a National Stage Application under 35 U.S.C. § 371 of PCT International Application No. PCT/IB2015/053518 which has an International filing date of May 13, 2015, the entire contents of which are hereby incorporated by reference.

The present invention relates to a method for determining an indication of wholesomeness of an item of packaged food or drink.

The term 'wholesomeness', as used herein, shall be understood to mean suitability for consumption. The phrase 'an indication of wholesomeness' shall be understood to mean an indication of one or more physical or chemical properties of an item of food and/or drink that is indicative of its wholesomeness and may be, for example, indicative of its freshness, its maturity and/or its safety for consumption. The term 'aliment' as used herein shall be understood to mean an item of one or both food and drink as the context demands. Other grammatical forms of the terms and phrases shall be interpreted accordingly.

The wholesomeness of aliments, in general, is a long standing consumer and commercial concern. Even if a particular aliment was wholesome at the point of packaging or at the point of sale to a consumer it's wholesomeness at the time of purchase or consumption by the consumer cannot be readily determined.

One attempt to ensure that the aliment is wholesome at the time of consumption is the now almost mandatory use of so called 'use-by dates', 'sell-by dates' or 'best-before dates'. (For ease of reference these will be commonly referred to hereinafter as 'indicator dates') which are printed on the aliment's packaging. As a consequence of the general reliance on indicator dates the food industry, when establishing such a date, has to add a significant safety margin to it to ensure that substantially all items in a particular lot of the packaged aliment will be fit for consumption at that date (provided of course that the items are handled according to instructions or common best practice). This way of establishing an indicator date does not take into account the actual state of the individual packaged aliments in a production batch. Rather, it represents a safe, hence generally short, time interval during which all individually packaged aliments from within a batch can be expected to be wholesome. This results in the selection of an indicator date to ensure that it will cover a hypothetical 'worst-case' item in the batch. Consequently, many of the actual items of packaged aliment in a batch are perfectly wholesome but are discarded none the less when the indicator date is reached, which is a wasteful practice.

The reliance on indicator dates as a guarantee of wholesomeness can, conversely, lead to an item of a packaged aliment appearing to be wholesome because its indicator date has not been reached whereas in reality the item has become unwholesome. For example, detrimental circumstances, often related to improper transportation and/or storage of the aliment, may occur. Such circumstances can negatively affect the wholesomeness of the aliment, for example through unwanted microbial decay, and as a result the item of packaged aliment may become unwholesome before the indicator date has been reached.

An aliment may also become unwholesome for safety reasons if for example the item has been subjected to tampering through illegal introduction of agents such as drugs or toxic chemicals after packaging. In such illegal circumstances the indicator date is of no use.

Presently quality control of the packaged aliment, for example either by governmental controlling authorities or stakeholders in the logistic supply chain (such as manufacturers, shippers, wholesalers or retailers), is performed at least partly in an attempt to detect if the aliment is unwholesome as a consequence of such detrimental circumstances. However, present quality control procedures inevitably involve opening the packaging of selected items of packaged aliment from within a batch in order to analyse the aliment inside. Once open these selected items loose most of their commercial value and are at best recycled but more likely they are disposed of. In order to minimise waste and to generally reduce the cost of food inspection, quality control is performed on a limited number of randomly selected items from a batch of packaged aliment. This cannot offer any guarantee that every item in the batch exhibits the desired wholesomeness.

It is known from WO 2015036399 of Johann Angres to interrogate examples of packaged aliments at discrete time intervals in a process to establish a generic shelf-life value (or indicator date, as used herein) to be generally applied to all examples of such packaged aliments. Only when the interrogation reveals that changes to the packaged aliment lies outside predefined boundaries is the package opened and a direct measurement of properties of the particular aliment performed. Thus the number of packages needed to be opened is reduced.

Furthermore it is known from US 2013/0112895 of Birlouez-Aragon et al. to employ an analysis of the optical natural fluorescence spectra of a sample obtained from a packaged aliment in order to obtain an indication of wholesomeness without reference to indicator dates. According to this disclosure an individual sample is unpacked and spectral information is compared mathematically, typically using a prediction model developed using a multivariate or multipath analysis method, with information derived from a plurality of generic reference spectra of wholesome samples in order to obtain an indication of wholesomeness of the aliment being analyzed.

One problem with the approach described in US 2013/0112895 is that the comparison is still with a set of generic reference data.

Another problem is that the packaging is necessarily compromised in order to extract a sample. This practice, as mentioned above, most often leads to the waste of the entire item of packaged aliment and can only be applied to a limited number of items in a batch lest the entire batch be destroyed.

There exists a need for a method of determining an indication of wholesomeness of an item of packaged food or drink without breaking the package, and which may, in some applications and embodiments, be applied at one or more points throughout the logistics supply chain, by manufacturer, shipper, wholesaler, retailer or consumer.

According to the present invention there is provided a method for the non-intrusive determination of an indication of wholesomeness of an unopened item of packaged aliment comprising the steps of: illuminating an unopened item of packaged aliment with electromagnetic energy at a plurality of different wavelengths through a suitably transparent region of the packaging so as to interact with the packaged aliment; obtaining spectral information regarding the interaction of the plurality of different wavelengths with the packaged aliment as subsequent spectral information; and interrogating the packaging to provide access to original spectral information regarding a previous interaction of the plurality of wavelengths with the same item of packaged aliment for the determination of an indication of wholesomeness from a measure of a spectral deviation between the original spectral information and the subsequent spectral information.

The method according to the present invention may also comprise the steps of: comparing some or all of the subsequent spectral information with some or all of the original spectral information to obtain a measure of their spectral deviation; and determining an indication of wholesomeness of the unopened item of packaged aliment in dependence of the obtained measure of spectral deviation, which steps may be performed by the same or a different person or entity that performed the previous steps.

The method according to the present invention may also comprise the steps of: initially illuminating the item of packaged aliment with electromagnetic energy at at least the plurality of different wavelengths through the suitably transparent region of the packaging so as to interact with the packaged aliment; obtaining spectral information regarding the interaction of the plurality of different wavelengths with the packaged aliment as the original spectral information; and associating the original spectral information with the packaging for access by interrogating the packaging, which steps may be performed by a one or none of the party(ies) or entity(ies) performing any of the previous steps.

Changes in the chemical or physical state of an aliment typically indicate changes in that aliment that will ultimately affect its wholesomeness. It is well known that these chemical or physical changes may be manifest as changes in the spectral information from the aliment. Thus by monitoring over time the spectral information of an aliment certain chemical or physical dependent characteristics of that particular aliment may be determined and a dependent indication of wholesomeness of that individual aliment may be provided. The indication may, for example, be an indication of its general state (e.g. freshness as opposed to spoilage); its maturity (e.g. ripeness as opposed to over-ripeness); or its safety (e.g. the absence as opposed to presence of contaminants which may have either developed after packaging or been introduced through tampering).

Since the determination is made by comparing spectral information obtained from the same individual packaged aliment at different points in time then this determination is unique for a particular item of packaged aliment and thus problems associated with the generalisations imposed by the reliance on either indicator dates or generic reference spectral data may be avoided.

Performed in such a manner the determination is non-intrusive and so does not reduce the commercial value of the aliment items due to broken packaging. Quality control may, if so wished, be performed on a large number of items, even every item, in a batch of packaged aliments. Also, determinations in respect of a single item of packaged aliment may be made repeatedly, for example at different stages (hence at different geographical locations) in the logistics supply chain to thereby increase confidence that the item of packaged aliment is in a condition that a manufacturer would wish it to be all the way to the point of consumption.

In order to improve the accuracy of any determination the plurality of wavelengths of electromagnetic energy should advantageously be able to pass through the suitably transparent region of the packaging that is formed by some or all of the packaging material, e.g. a suitably transparent window provided in an otherwise opaque packaging material, with minimal and reproducible optical distortion both before and after interaction with the aliment in the unopened packaging. It will be appreciated that by 'suitably transparent' it is meant transparent to at least the plurality of different wavelengths intended for illuminating the unopened item of packaged aliment.

Usefully a machine readable tag is attached to the packaging to enable retrieval and/or association of the original spectral information specific to the packaged item. This tag may, for example, be an electronic tag, such as a RFID chip, comprising an addressable memory holding the original spectral information for uploading to an addressable memory of a data processor. The tag may additionally or alternatively provide a hyperlink to the original spectral information stored on a remotely accessible storage device, such as on a server, and may be constituted in an optical machine readable representation as provided by a barcode of the linear (e.g. EAN code) or the matrix (e.g. QR™ code) type attached to the packaging through printing.

These as well as other features and advantages of the present invention will be better understood through a consideration of the following illustrative and non-limiting detailed description of an embodiment of the present invention, made with reference to the drawing of the appended FIGURE:

FIG. 1 Shows a flow chart representation of an embodiment of the method according to the present invention.

With reference to FIG. 1, an exemplary application of the method according to the present invention is disclosed. Initially in step 110 the spectrometer to be used is standardized to ensure that the spectral response from the spectrometer used to collect original spectral information at step 120 is compatible with the response from the spectrometer used to collect subsequent spectral information at step 140 assuming that these spectrometers are not the same instrument. To achieve standardized instruments different methods are available. The instruments can be standardized from factory by using the same hardware design and using optical standards to ensure comparable response from different instruments. If instruments of different design are to be standardized well defined optical standards or natural products can be measured on both instruments under strictly controlled conditions, and the observed spectral differences can be used to mathematically modify the response from one of the instruments to resemble the response from the other. Renewed standardization is not required for each sequence of collection of spectral information but the compatibility of the response from different instruments must be confirmed at regular intervals.

Original spectral information is obtained at an initial collection step 120 from detecting electromagnetic energy at a plurality of different wavelengths, preferably at infrared and more preferably near infrared wavelengths, after it having illuminated and subsequently interacted with an item of packaged aliment. The aliment is illuminated through a suitably transparent region, such as an optical window, in the packaging material. In other embodiments the majority, if not all, of the packaging material forms the suitably transparent region. The electromagnetic energy interacts with the aliment and some of it transformed before passing back through the transparent region of the packaging to be detected using a spectrometer. The electromagnetic energy may consist of a plurality of discrete wavelengths or wavelength bands, or may be continuous across a wavelength region of interest.

If the aliment is intended to remain essentially unchanged inside of the packaging until sold to or used by a consumer, the collection of original spectral information of the aliment inside of the packaging is preferably done when the aliment is as fresh as possible which normally is immediately after packaging. If the aliment is intended to be sold in a mature (or ripe) state, the collection of original spectral information of the aliment inside of the packaging may preferably be postponed until the ripening process has progressed to a suitable degree.

By way of example, the initial collection step 120 here comprises the detection of variations in the intensities of the illuminating wavelengths after their interactions with the aliment inside of the packaging using a conventional spectrometer and storing, as the original spectral information, a representation of the detected wavelength dependent intensity variations indexed against wavelength in a form that may be manipulated in a data processor.

At step 130 the original spectral information which was obtained at step 120 is associated with the specific item of packaged aliment from which this original spectral information was obtained and stored for subsequent use. The association may be via an identity code that is unique to that packaged aliment. In the present embodiment a machine readable tag is fixed on to the packaging and used to provide this association. This tag, in one embodiment, includes a memory portion in which the original spectral information is stored along with metadata identifying the aliment and which can be interrogated in order to retrieve the information for subsequent use in a data processor. In another embodiment the spectral information is stored on a remotely accessible storage device together with information identifying the specific item of aliment, enabling subsequent access to the original spectral information and metadata by means of a unique hyperlink established by means of a linear or matrix type barcode printed on the packaging.

At one or several later points in time subsequent spectral information is generated in step 140 for the unopened item of packaged aliment in a manner analogous with the generation of original spectral information at step 120 for the same unopened item of packaged aliment. In the present example this subsequent spectral information is thus collected by illuminating the aliment through the suitably transparent portion of the packaging material, such as an optical window in the packaging material, with electromagnetic energy of the same plurality of wavelengths that were employed at step 120 and detecting their interaction with the packaged aliment using a second spectroscopic instrument. In an embodiment this subsequent spectral information has the same form as the original spectral information that was obtained at step 120 and in the present example the subsequent spectral information is a representation of the detected wavelength dependent intensity variations indexed against wavelength in a form that may be manipulated in a data processor.

Retrieval of the original spectral information in step 150 may be performed either before or after the collection of subsequent spectral information in step 140 and here comprises the interrogation of the machine readable tag by a tag reader in order to provide access the original spectral information. In an embodiment where the machine readable tag comprises a memory in which the original spectral data is stored the tag reader operates at this interrogation step 150 to upload the stored original spectral information into an addressable memory accessible to a data processor. In another embodiment where the machine readable tag provides a hyperlink to the original spectral information specific to the item of packaged aliment, the data processor may also include remote communication functionality such as may be provided by known computer network adaptors of either software or hardware types.

At step 150 the original spectral information and the metadata identifying the item of packaged aliment are then downloaded to the addressable memory for further processing by the data processor as will be described below. Alternatively metadata identifying the item of packaged aliment and usefully, the subsequent spectral information, may be uploaded to the remote server to which the hyperlink was established. The corresponding original spectral information is then accessed at the remote server and in one embodiment may be further processed remotely at this server with the results of the processing being transmitted from the server to the network adaptor of the data processor or to another remote communications device, typically for presentation to a user. It will be appreciated that the server may reside at a single location or at a plurality of remote locations interconnected to provide the functionality described above.

The original spectral information and the subsequent spectral information from the same packaged aliment are compared in the data processor or at the remote server at step 160 in order to obtain a measure of spectral deviation between the spectral information obtained from two different points in time. Since the original and the subsequent spectral information are collected from the same packaged aliment the deviation between the two sets of spectral information represent changes to the same item of aliment over time. This has an advantage over known methods that spectral interference from comparing two different items of aliments which are slightly spectrally different even if they are of the same type is avoided.

At step 160 the spectral deviation may be calculated in the data processor or at the server by subtracting the subsequent spectral information regarding an intensity value at each of the plurality of wavelengths from the original spectral information regarding an intensity value at the corresponding wavelengths. Alternatively more sophisticated algorithms for spectral pre-processing or spectral compression may be applied to the spectral information in order to enhance the effect of physical or chemical changes to the aliment itself on the spectral deviation using techniques well-known to the field of chemometrics.

The desired indication of wholesomeness of the aliment, such as freshness, may, for example, be made using the spectral deviation calculated at step 160 for the specific item of packaged aliment being analyzed and simply comparing this spectral deviation with those stored in a look-up table by which values of spectral deviations are indexed against a degree of wholesomeness obtained from measurements on reference samples. In the present embodiment and more preferably the spectral deviation calculated at step 160 is used as input to an empirical prediction model encompassing comparable spectral deviations observed for a population of similar items of the same type of aliment which have been exposed under controlled conditions to factors alone or in combination and known to affect wholesomeness. The formation of such a wholesomeness prediction model is described with reference to steps 170 through 260.

At step 170 a representative batch of fresh aliment items ('reference samples') intended for inclusion in a wholesomeness library being of the same type as the aliment for which the indication of wholesomeness is to be determined are subjected to so-called 'reference analyses' to determine wholesomeness of each of the items. These reference analyses are typically conducted just prior to packaging and are typically performed with the same kind of analysis techniques that are routinely used for quality control of the type of aliment in question such as one or a combination of chemical analysis, microbiological analysis, organoleptic assessment, spectroscopic analysis or chromatographic analysis.

In step 180 the spectrometer or spectrometers to be used for collecting spectra from the reference samples should preferably be standardized as described in step 110 to ensure that the spectral response from the spectrometer(s) used to collect original spectral information at step 190 is compatible with the response from the spectrometer(s) used to collect subsequent spectral information at step 210 as well as with the spectrometer(s) used in steps 120 and 140 for analyzing an unknown item of aliment, assuming that these spectrometers are not one and the same.

After packing, original spectral information is collected in step 190 from each of the reference samples intended for inclusion in the library through the suitably transparent portion of the packaging, such as an optical window in the packaging, using the same plurality of wavelengths and the same spectral techniques as in steps 120 to 140. The original spectral information is normally collected immediately after packaging but if the aliment is intended to be sold in a mature (or ripe) state the collection of original spectral information of the aliment inside of the packaging may preferably be postponed until the ripening process has progressed to a suitable degree.

At step 200 each of the reference samples is subjected in a controlled manner to one or a combination of several factors known to affect the wholesomeness in either a detrimental manner where wholesomeness is deteriorating or in a beneficial manner where wholesomeness is improved through ripening or maturation. Typical factors include storage time, storage temperature, temperature fluctuations during storage, light exposure during storage, imperfect packaging and tampering agents. The effect of a given factor shall be varied between the reference samples of the packaged aliment to be included in the library to encompass changes of wholesomeness both inside and beyond of what is acceptable, desirable and safe for the type of aliment at various points through the chain of logistics and when sold for final consumption.

At step 210 after having been subjected to one or more factors affecting wholesomeness subsequent spectral information from each of the items in the batch of reference samples of the packaged aliment intended for the library is collected through the suitably transparent portion of the packaging using the same plurality of wavelengths and the same spectral techniques that were used in step 190.

At step 220 the wholesomeness of each of the reference samples is determined again using the same reference analysis technique or combination of reference analysis techniques that were used in step 170. This step should be performed within a time-span after step 210 which is sufficiently small to ensure that no detectable change in wholesomeness occurs between the measurements performed at these steps 210 and 220 and therefore that the subsequent spectral information collected in step 210 properly reflects the wholesomeness determination at this step 220.

It will be appreciated that the reference analysis at step 220 will require the package of each of the items in the batch constituting the reference samples to be opened, making the items in question unfit for subsequent manipulations. For factors where the effect is to be studied in several steps or intervals, for example different storage times, separate batches of aliment items intended as reference samples will therefore be required. It will also be appreciated that the principle of non-intrusive determination of wholesomeness applies to unknown items of aliments but not to the batches of items of aliment constituting reference samples intended for the wholesomeness library.

The original spectral information collected at step 190 from a particular batch of items intended as reference samples and the subsequent spectral information from step 210 from the same batch of reference samples are compared at step 230 in order to obtain a measure of deviation of spectral information for each reference sample as affected by the factor or factors under study. The algorithms used to determine the spectral deviation between the original and the subsequent spectral information must be identical with those used for the unknown aliment in step 160.

The original referenced values collected at step 200 from a particular batch of reference samples and the subsequent reference values from step 220 from the same batch of reference samples are compared at step 240 in order to obtain a measure of reference value deviation for each reference sample as affected by the factor or factors under study.

Steps 170 to 240 can be repeated with additional batches of reference samples of the same type of aliment in order to study the effect of other steps or intervals of a particular factor, other factors or a combination of other factors on the wholesomeness of such items.

In step 250 the outcome from all of batch studies of reference samples in the form of spectral deviations with corresponding reference value deviations representing the factors investigated is amalgamated in a wholesomeness library for the type of aliment in question.

In step 260 a wholesomeness prediction model describing the empirical relation between the sets of spectral deviations and the corresponding sets of reference value deviations is developed using linear or non-linear mathematical techniques well-known to the field of chemometrics.

In step 270 the spectral deviation of the packaged aliment from step 160 is used as input to the wholesomeness prediction model from step 260. This wholesomeness prediction model may reside on the data processor or at the remote server.

The output from the prediction model in step 280 will be one or a plurality of estimates of reference value deviations which in turn indicate the state (or degree) of wholesomeness of the unknown packaged aliment. The final output can be a simple indicator describing the degree of wholesomeness in terms such as "fresh", "still fresh for a limited period of time", or "no longer fresh". In addition the reason for a would-be unwholesomeness in the unknown packaged aliment can be predicted in those cases where the spectral deviation corresponds to similar deviations in the wholesomeness library caused by a particular factor of influence (for example "Too high storage temperature" or "Risk of tampering"). In such cases where the changes to wholesomeness are desired the output can additionally or alternatively be a prediction of the state or degree of ripeness.

It will be appreciated that collection and association of the original spectral data as described with reference to steps 110 to 130 of FIG. 1 may be performed at one location by a first party and the collection of subsequent spectral data and its use in establishing the indication of wholesomeness as described with reference to steps 140 to 160 and steps 270 to 280 of FIG. 1 may be performed at one or more other locations by one or more other parties. Thus it will be understood that the method according to the present invention for determining an indication of wholesomeness relies only on access to the original spectral data and the subsequent spectral data, irrespective of how and when they were obtained. Similarly the origination of the empirical relationship to be employed in determining an indication of wholesomeness need not, indeed typically is not, done by the same entity or person determining the indication. Also, obtaining the measure of spectral deviation and the determination of the indication of wholesomeness from the obtained measure need not be done by the same person or entity as one or more of the origination of the empirical relationship, the collection and association of original spectral data and the collection of subsequent spectral data.

The invention claimed is:

1. A method for performing a non-intrusive determination of an indication of wholesomeness of a particular unopened item of packaged aliment, the method comprising:
    illuminating the particular unopened item of packaged aliment with electromagnetic energy at a plurality of different wavelengths through a transparent portion of packaging of the particular unopened item of packaged aliment to cause the electromagnetic energy to interact with the packaged aliment;
    obtaining spectral information regarding the interaction of the plurality of different wavelengths with the particular unopened item of packaged aliment as subsequent spectral information based on the illuminating;
    examining a portion of the packaging of the particular unopened item of packaged aliment to identify an identity code that is uniquely associated with the particular unopened item of packaged aliment, the identity code further associated with a particular instance of original spectral information regarding a previous interaction of electromagnetic energy at the plurality of different wavelengths with the particular unopened item of packaged aliment;
    obtaining the particular instance of original spectral information based on processing the identity code; and
    determining an indication of a degree of wholesomeness of the particular unopened item of packaged aliment based on a determination of a spectral deviation between the particular instance of original spectral information and the subsequent spectral information, the determination of the spectral deviation based on application of an empirical relationship to the spectral deviation, the empirical relationship includes an association of values of spectral deviation with degrees of wholesomeness of unopened items of packaged aliment.

2. A method as claimed in claim 1, further comprising:
    comparing at least a portion of the subsequent spectral information with at least a portion of the particular instance of original spectral information to determine the spectral deviation.

3. A method as claimed in claim 1, further comprising:
    initially illuminating the particular unopened item of packaged aliment with the electromagnetic energy at the plurality of different wavelengths through the transparent portion of the packaging to cause the electromagnetic energy to initially interact with the packaged aliment;
    obtaining spectral information regarding the initial interaction of the plurality of different wavelengths with the particular unopened item of packaged aliment as the particular instance of original spectral information; and
    generating the identity code associating the particular instance of original spectral information with the packaging of the particular unopened item of packaged aliment for access based on examining the packaging.

4. A method as claimed in claim 1, wherein examining the packaging includes examining a machine readable tag attached to the packaging.

5. A method as claimed in claim 4, wherein examining the machine readable tag includes uploading the particular instance of original spectral information into an addressable memory of a data processor from a memory portion of the machine readable tag.

6. A method as claimed in claim 4, wherein examining the machine readable tag includes
    reading a barcode to acquire information indicating a hyperlink to the particular instance of original spectral information stored on a remotely accessible storage device; and
    following the hyperlink to access the particular instance of original spectral information.

7. A method as claimed in claim 1, wherein the determined indication of the degree of wholesomeness is at least one indication of a freshness indication, a maturity indication, and a safety indication.

8. A method as claimed claim 1, wherein the empirical relationship includes a look-up table, the look-up table including measured values of spectral deviation, determined using measurements on reference samples, indexed against degrees of wholesomeness determined using measurements on the reference samples.

9. A method as claimed in claim 1 wherein the empirical relationship includes a prediction model that includes an association of measured values of spectral deviation, determined using measurements on reference samples, against degrees of wholesomeness determined using measurements on the reference samples.

10. A method as claimed in claim 3, further comprising:
    obtaining the particular instance of original spectral information at a first geographical location; and
    obtaining the subsequent spectral information at one or more second geographical locations that are different from the first geographical location.

* * * * *